United States Patent [19]
Albert et al.

[11] Patent Number: 5,866,356
[45] Date of Patent: Feb. 2, 1999

[54] PROTECTIVE HOUSING FOR BIOLOGICAL INDICATOR FOR TESTING THE EFFECTIVENESS OF A STERILIZATION PROCEDURE

[75] Inventors: Heidemarie Albert, Johannesburg, South Africa; William F. Foltz, Cottage Grove; Lewis P. Woodson, Apple Valley, both of Minn.

[73] Assignee: Minnesota Mining and Manufacturing Company, St. Paul, Minn.

[21] Appl. No.: 954,218

[22] Filed: Oct. 20, 1997

[51] Int. Cl.[6] .............................. C12Q 1/22; C12Q 1/00; G01N 21/00
[52] U.S. Cl. .................... 435/31; 435/4; 435/283.1; 422/50; 422/56; 422/58
[58] Field of Search ................. 435/31, 4, 283.1; 422/50, 56, 58

[56] References Cited

U.S. PATENT DOCUMENTS

| | | | |
|---|---|---|---|
| 3,239,429 | 3/1966 | Menolasino et al. | 195/54 |
| 3,440,144 | 4/1969 | Andersen | 195/103.5 |
| 3,661,717 | 5/1972 | Nelson | 195/103.5 |
| 4,115,068 | 9/1978 | Josyln | 422/56 |
| 4,145,186 | 3/1979 | Andersen | 23/232 |
| 4,240,926 | 12/1980 | McNeely | 252/408 |
| 4,304,869 | 12/1981 | Dyke | 435/296 |
| 4,311,793 | 1/1982 | Halleck | 435/31 |
| 4,486,387 | 12/1984 | Augurt | 422/58 |
| 4,576,795 | 3/1986 | Bruso | 422/58 |
| 4,579,715 | 4/1986 | Bruso | 422/58 |
| 4,580,682 | 4/1986 | Gorski et al. | 206/569 |
| 4,594,223 | 6/1986 | Dyke et al. | 422/56 |
| 4,596,696 | 6/1986 | Scoville, Jr. | 422/61 |
| 4,636,472 | 1/1987 | Bruso | 435/287 |
| 4,650,479 | 3/1987 | Insley | 604/358 |
| 4,692,307 | 9/1987 | Bruso | 422/58 |
| 4,699,765 | 10/1987 | Hambleton | 422/57 |
| 4,739,881 | 4/1988 | Bruso | 206/305 |
| 4,755,178 | 7/1988 | Insley et al. | 604/367 |
| 4,828,797 | 5/1989 | Zwarun et al. | 422/55 |
| 4,839,291 | 6/1989 | Welsh et al. | 435/296 |

(List continued on next page.)

FOREIGN PATENT DOCUMENTS

| | | |
|---|---|---|
| 647041 | 3/1991 | Australia . |
| 676743 | 12/1994 | Australia . |
| 0 254 428 A | 1/1988 | European Pat. Off. . |
| 0 255 229 A2 | 2/1988 | European Pat. Off. . |
| 0 419 282 B1 | 3/1991 | European Pat. Off. . |
| 0 421 760 A1 | 4/1991 | European Pat. Off. . |
| WO 94/28164 | 12/1994 | WIPO . |

OTHER PUBLICATIONS

D.J.R. Laurence, *Fluorescence Techniques for the Enzymologist*, Methods in Enzymology, vol. 4, S. P. Colowick and N.O. Kaplan, Eds., Academic Press, New York, 1957.
M. Roth, *Methods of Biochemical Analysis*, vol. 17, D. Block, Ed., Interscience Publishers, New York, 1992.
S. Udenfriend, *Fluorescence Assay in Biology and Medicine*, Academic Press, New York, 1962.
*The Merck Index*, (12th Edition 1996), p. 1425.

*Primary Examiner*—Louise N. Leary
*Attorney, Agent, or Firm*—Robert W. Sprague

[57] ABSTRACT

A protective housing for a biological indicator for testing the effectiveness of a sterilization procedure comprises a tube constructed of a liquid impermeable and gas-nonabsorptive polymer, a cap assembly having an aperture that allows sterilant to enter the housing during the sterilization procedure and contact the biological indicator, and an absorptive material in the cap assembly to prevent condensed sterilant from entering the housing and contacting the biological indicator. During a sterilization procedure the protective housing reduces premature inactivation of biological indicators, especially biological indicators that measure the effectiveness of a sterilization procedure by monitoring an enzyme whose activity can be correlated with the viability of at least one microorganism commonly used to monitor sterilization efficacy.

57 Claims, 6 Drawing Sheets

U.S. PATENT DOCUMENTS

| | | | |
|---|---|---|---|
| 4,863,867 | 9/1989 | Joyce et al. | 435/287 |
| 4,883,641 | 11/1989 | Wicks et al. | 422/50 |
| 4,902,478 | 2/1990 | Hambleton | 422/56 |
| 4,918,003 | 4/1990 | Macaro et al. | 435/31 |
| 4,985,298 | 1/1991 | Buckley et al. | 428/288 |
| 5,024,865 | 6/1991 | Insley | 428/36.4 |
| 5,073,488 | 12/1991 | Matner et al. | 435/31 |
| 5,217,901 | 6/1993 | Dyckman | 435/291 |
| 5,219,504 | 6/1993 | Insley | 264/116 |
| 5,223,401 | 6/1993 | Foltz et al. | 435/18 |
| 5,252,484 | 10/1993 | Matner et al. | 435/288 |
| 5,418,167 | 5/1995 | Matner et al. | 435/288 |
| 5,460,880 | 10/1995 | Patnode et al. | 428/354 |
| 5,486,459 | 1/1996 | Burnham et al. | 435/31 |
| 5,516,648 | 5/1996 | Malchesky et al. | 435/31 |
| 5,518,763 | 5/1996 | Patnode et al. | 427/208 |
| 5,577,494 | 11/1996 | Kuypers et al. | 128/201 |

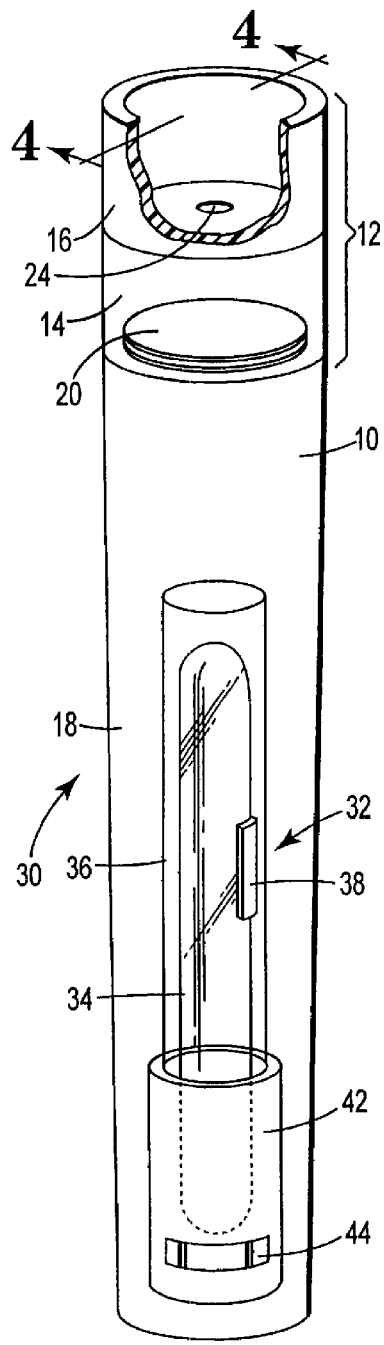
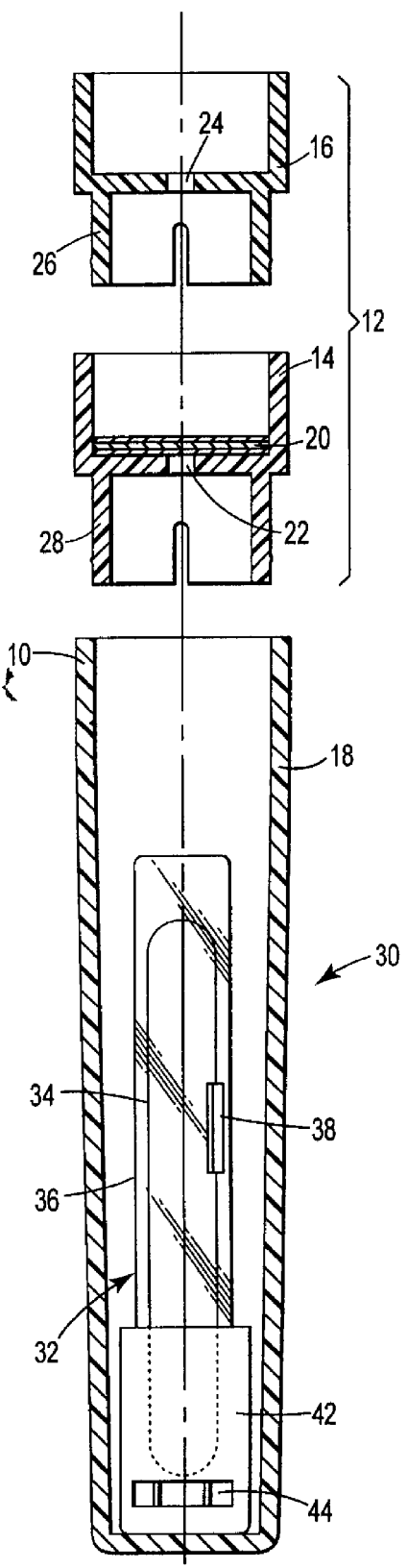
Fig. 3
Fig. 4

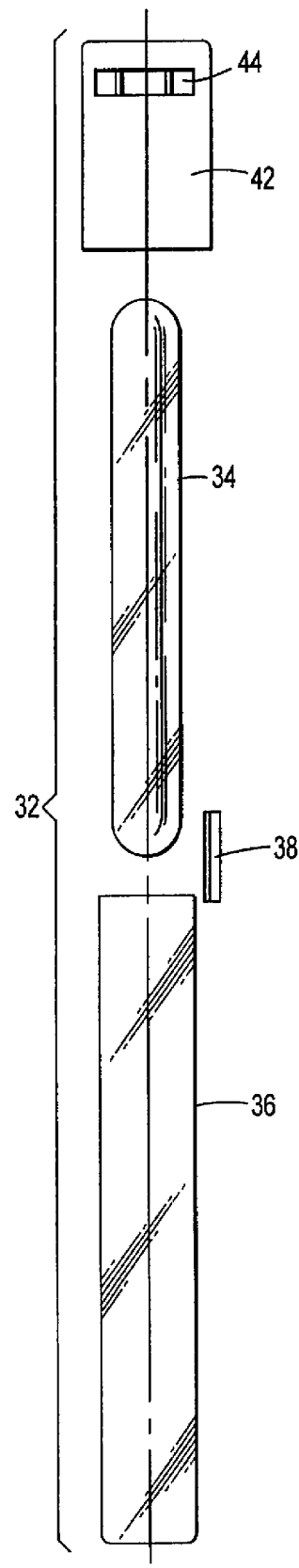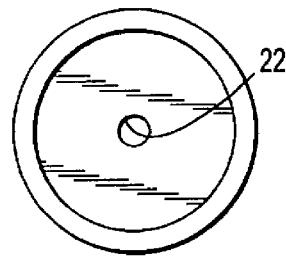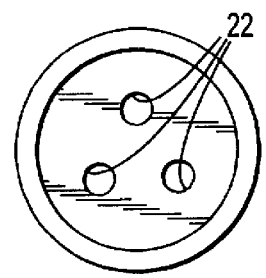
Fig. 5
Fig. 6
Fig. 7

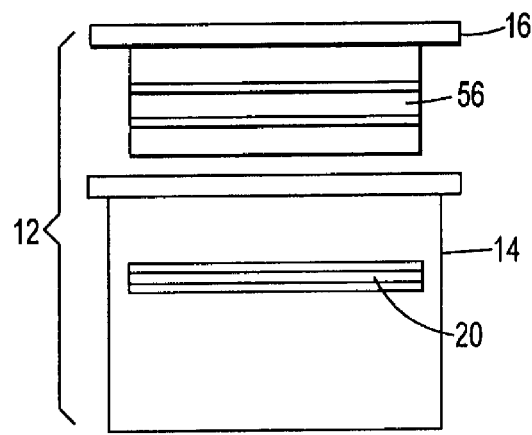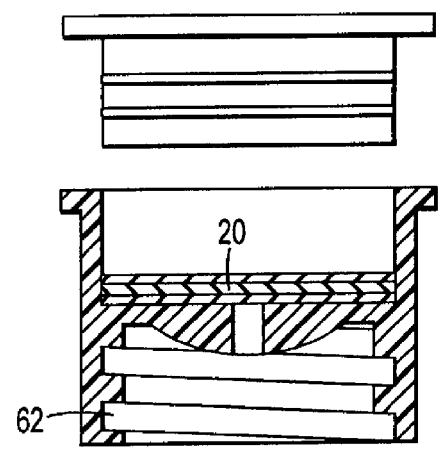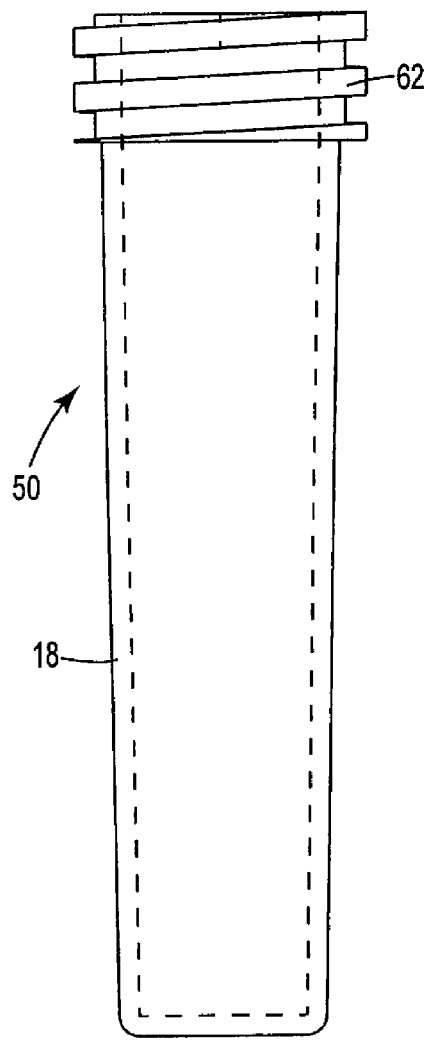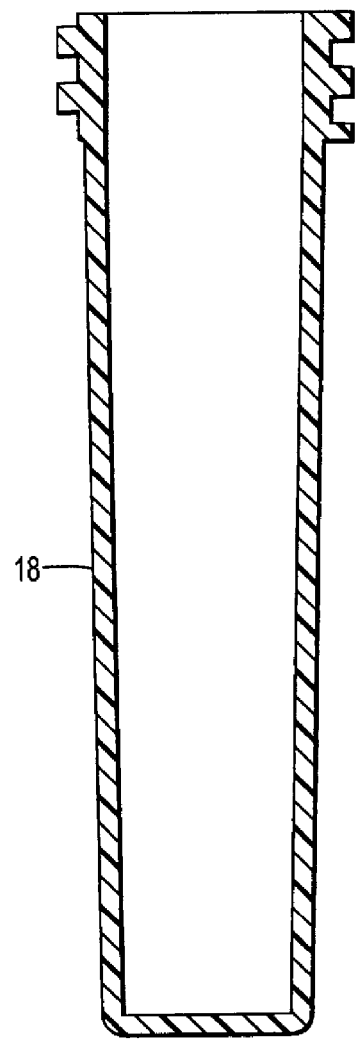
Fig. 8
Fig. 9

PROTECTIVE HOUSING FOR BIOLOGICAL INDICATOR FOR TESTING THE EFFECTIVENESS OF A STERILIZATION PROCEDURE

FIELD OF THE INVENTION

The present invention relates to biological indicators for testing the effectiveness of a sterilization procedure. In particular, the invention relates to a protective housing for a biological indicator and to a method of using the protective housing to test the effectiveness of a sterilization procedure. The protective housing includes a tube to contain a biological indicator and a cap assembly designed to prevent condensed sterilant from contacting the biological indicator within the tube. The cap assembly includes an aperture through which non-condensed sterilant may enter the housing to contact the biological indicator. An absorbent material within the cap assembly retains condensed sterilant and inhibits fluid from entering the tube and contacting the biological indicator, yet allows noncondensed sterilant to enter the housing.

BACKGROUND

Biological indicators are recognized in the art as providing an accurate and precise means for testing the effectiveness of a sterilization procedure. Conventional biological indicators gauge the effectiveness of a sterilization cycle by monitoring the survival of a test microorganism that is many times more resistant to the sterilization process than most organisms that would be present by natural contamination. The biological indicator is exposed to a sterilization cycle and then incubated under conditions that will promote the growth of any surviving test microorganisms. If the sterilization cycle fails, the biological indicator generates a detectable signal that the biological specimen survived. The detectable signal may, for example, be luminescent, fluorescent, color or radiation.

One well-known type of biological indicator uses spores from bacteria or fungi to test the effectiveness of a sterilization procedure. Biological indicators of this type commonly employ a nesting tube arrangement, in which a smaller inner tube that contains spore growth media nests within a larger tube having a gas-permeable cap. The inner tube is made of glass or some other frangible material and is completely sealed. The outer tube is made of a compressible plastic. The spores are impregnated upon filter paper or some other appropriate carrier, which is located between the walls of the outer and inner tubes during the sterilization procedure. The sterilant enters this void through the cap and contacts the spores during the sterilization procedure. Afterward the inner tube is broken, exposing the spores to the growth media. The biological indicator is then incubated in conditions that promote the growth of viable spores. If spores survive the sterilization cycle, a pH indicator in the growth medium will change color, indicating that the sterilization cycle has failed. Although accurate, biological indicators that rely on the growth of spores are slow, commonly requiring between 1 and 7 days to give final results. During the incubation period, the goods must be quarantined, and a large amount of space must be committed to their storage.

More recently biological indicators have been developed that measure the effectiveness of sterilization cycles by monitoring an enzyme whose activity can be correlated with the viability of at least one microorganism commonly used to monitor sterilization efficacy. In contrast to biological indicators that measure spore growth alone, enzyme indicators provide fast results, often in as little as one to three hours. If the sterilization procedure works properly, the enzyme will be inactivated during the cycle. If, however, the sterilization procedure fails, the enzyme will retain its activity and react with a substrate to form a detectable product. Enzyme biological indicators include a source of active enzyme and a substrate that reacts with the enzyme. The enzyme and substrate are separated from each other by a physical barrier during the sterilization cycle, and are mixed together afterward. The formation of an enzyme-substrate product is detectable as a fluorescent or color change. Enzyme biological indicators are described in U.S. Pat. No. 5,073,488, which is incorporated in its entirety herein by reference.

Enzyme biological indicators may be used alone or as part of a dual biological indicator. Dual biological indicators are enzyme biological indicators that measure both enzyme activity and spore growth to determine the effectiveness of a sterilization cycle. The enzyme system gives rapid results, which are then confirmed by measurement of spore outgrowth. In a dual biological indicator the spores themselves may be the source of active enzyme. 3M™ Attest™ 1291 and 1292 Rapid Readout Biological Indicators, available from 3M Company, St. Paul, Minn., are dual indicators that measure both enzyme activity and the growth of live spores.

Although enzyme biological indicators are both rapid and accurate for most uses, it has been observed that when certain pre-vacuum, or vacuum assisted, steam sterilization protocols are followed the enzyme may be prematurely inactivated, leading to false indications of sterility or false negatives. When these sterilization procedures are used, dual indicators may show positive signs of spore growth even though the indicator showed no signs of enzyme activity. This is not a problem in the United States, where steam is introduced to the sterilization chamber before a vacuum is drawn. However, in Europe, where pre-vacuum sterilizers often draw a vacuum before steam is introduced, it is known that the enzyme is sometimes inactivated before the spores are killed. When this occurs, the enzyme is unable to form an enzyme-substrate complex that indicates that the sterilization cycle has failed, and contamination goes undetected. Although the precise mechanism underlying this problem is not known with certainty, it is believed that in European pre-vacuum cycles condensed sterilant contacts the enzyme and inactivates it.

There is a need for a protective housing for a biological indicator that will prevent condensed sterilant from contacting the biological indicator and inactivating it prematurely, but that will allow noncondensed sterilant to enter the housing and contact the biological indicator.

SUMMARY OF THE INVENTION

The present invention provides a protective housing for a biological indicator for testing the effectiveness of a sterilization procedure. The protective housing includes a material that absorbs condensed sterilant and thereby impedes it from contacting and prematurely inactivating the biological indicator, thus addressing a problem in the art. However, the housing does not prevent noncondensed sterilant in a gaseous or vapor state, such as steam, from entering the housing and contacting the biological indicator.

The protective housing for a biological indicator comprises a tube, a cap assembly and an absorbent material located within the cap assembly. The tube has open and closed ends and is made of a polymer that is liquid impermeable and gas nonabsorptive. The cap includes an opening for sterilant to enter the tube and an absorbent material to retain condensed sterilant. In a preferred embodiment, the cap has first and second portions and a sterilant access port through both portions. The first cap portion is adapted to couple with the second cap portion and with the open end of the tube. The absorbent material restricts the access of condensed sterilant to the biological indicator.

The present invention also includes a sterilization monitor assembly, which comprises the protective housing of the invention and a biological indicator. The biological indicator is located within the protective housing and produces a detectable signal if a sterilization procedure fails to establish a condition sufficient to kill a microorganism commonly used to monitor sterilization procedures.

The present invention further includes a method for testing the effectiveness of a sterilization procedure that makes use of the protective housing and the sterilization monitor assembly of the present invention. The method comprises the following steps: providing a sterilization monitor assembly for testing the effectiveness of a sterilization procedure including a protective housing and a biological indicator; subjecting the sterilization monitor assembly to a sterilization procedure; and examining the biological indicator for a detectable signal indicating that the sterilization procedure failed to kill substantially all contaminating microorganisms.

BRIEF DESCRIPTION OF THE FIGURES

FIG. 3 is a perspective view of a preferred embodiment of a sterilization monitor assembly of the present invention, with a portion of the cap assembly of the protective housing cut away to show the sterilant access port.

FIG. 4 is a partially exploded cross-sectional view of a preferred embodiment of a sterilization monitor assembly of the present invention.

FIG. 5 is an exploded view of a biological indicator used in preferred embodiments of the sterilization monitor assembly and the method of the present invention.

FIG. 6 is a top view of a cap assembly of a preferred embodiment of a protective housing of the invention, showing the sterilant access port.

FIG. 7 is a top view of a cap assembly of a preferred embodiment of a protective housing of the invention, showing the sterilant access port.

FIG. 8 is an exploded view of a preferred embodiment of a protective housing of the invention.

FIG. 9 is an exploded cross-sectional view of a preferred embodiment of a protective housing of the invention.

DETAILED DESCRIPTION OF THE INVENTION

The protective housing and sterilization monitor assembly of the present invention address a problem experienced with biological indicators that use enzymes to test the effectiveness of sterilization procedures. In particular, the protective housing and sterilization monitor assembly are designed to prevent, to the extent possible, condensed sterilant from contacting the enzyme in a biological indicator and inactivating it prematurely. It has been observed that when certain steam sterilization protocols are followed with dual indicators, the enzyme may be inactivated before the sterilization procedure has killed the test microorganism. When such an event occurs the biological indicator gives a false indication that the sterilization procedure was effective, or a false negative, when in fact contaminating microorganisms may have survived the cycle.

The protective housing of the present invention may be used in any type of sterilization procedure in which there is a risk that condensed sterilant will contact the biological indicator during the cycle and inactivate it. Sterilization procedures for which the protective housing may be used include procedures that use steam, hydrogen peroxide vapor phase, hydrogen peroxide-plasma, ethylene oxide gas, gas, dry heat, propylene oxide gas, methyl bromide, chlorine dioxide, formaldehyde and peracetic acid (alone or with a vapor phase), and any other gaseous or liquid agents. Although the protective housing is useful for many different types of sterilization procedures, the preferred use is as a housing for biological indicators in steam sterilization procedures. Most preferably, the protective housing is used in pre-vacuum steam sterilization cycles in which a vacuum is drawn in the sterilization chamber before steam is introduced.

Figure 11:
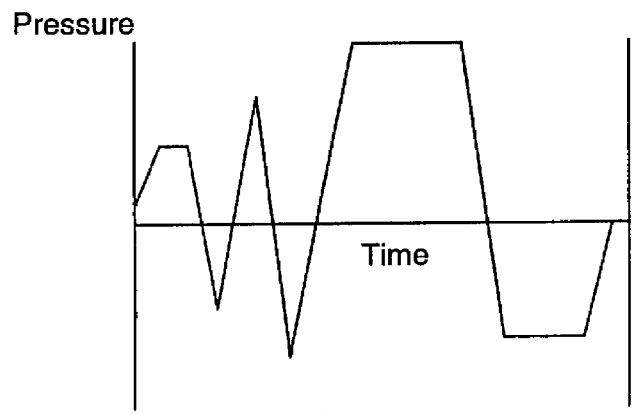
FIG. 11 is graph showing the change in pressure over time in a pre-vacuum sterilization cycle in which steam is injected into the sterilization chamber before a vacuum is pulled.

Dual indicators are used in several different steam sterilization cycles, but premature inactivation of enzyme is not a problem with all of them. It is primarily a problem with European pre-vacuum steam sterilization procedures. A pre-vacuum sterilization cycle is any sterilization cycle that uses a vacuum-driven conditioning phase before introduction of sterilant. In the pre-vacuum sterilization cycles most commonly used in the United States, steam is introduced into the sterilization chamber under pressure before a vacuum is drawn. FIG. 11 shows the pressure change over time in a representative pre-vacuum sterilization cycle of the type used in the United States. The initial pressure is positive as steam is injected, and then becomes negative as a vacuum is drawn. Commonly used sterilizing times and temperatures for pre-vacuum cycles are 132° C. for 3–4 minutes. Enzyme is inactivated just after spore kill in these cycles. Enzyme indicators provide accurate readings when used in these pre-vacuum steam cycles.

Figure 12:
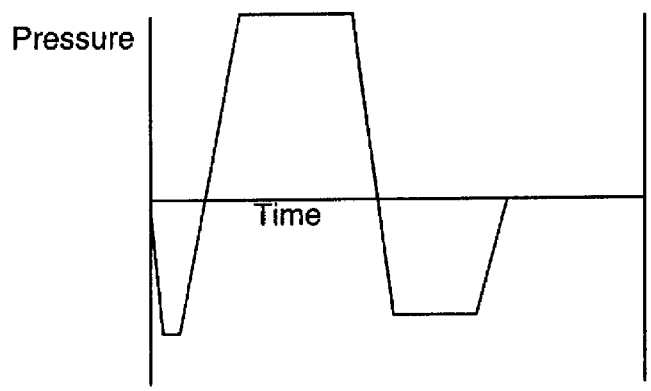
FIG. 12 is a graph showing the change in pressure over time in a pre-vacuum sterilization cycle in which a vacuum is pulled in one pulse before the introduction of steam into the sterilization chamber.
Figure 13:
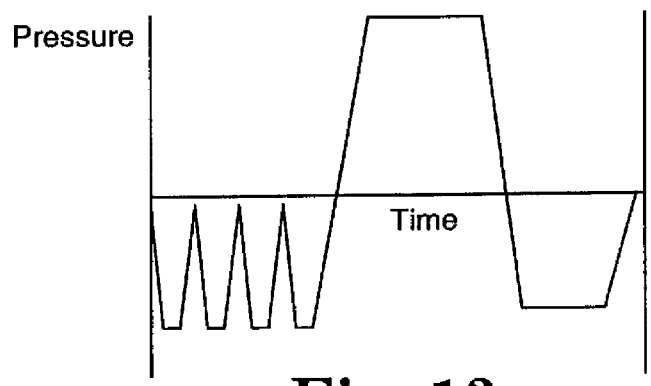
FIG. 13 is a graph showing the change in pressure over time in a pre-vacuum sterilization cycle in which a vacuum is pulled in four pulses before the introduction of steam into the sterilization chamber.

In contrast to the U.S. pre-vacuum cycles, steam cycles commonly used in Europe draw a vacuum in the sterilization chamber before steam is introduced. FIGS. 12–13 illustrate the change in pressure over time in two representative European pre-vacuum cycles. The cycle in FIG. 12 has one initial vacuum pulse before steam is injected, and the cycle in FIG. 13 uses four vacuum pulses. Enzyme biological indicators are sometimes prematurely inactivated in these cycles, leading to false negatives.

The protective housing of the present invention may be used with any type of biological indicator that is used to monitor the effectiveness of a sterilization cycle. Suitable biological indicators include indicators that use the growth of microorganisms such as spores to gauge the effectiveness of a sterilization procedure; indicators that use enzymes associated with microorganism growth to gauge the effectiveness of a sterilization procedure; and dual indicators, which use both an enzyme indicator and spore growth to measure the effectiveness of a sterilization procedure. In the most preferred embodiment of the invention, the protective housing is used with either an enzyme indicator or a dual indicator.

Enzyme biological indicators and dual indicators are described in U.S. Pat. No. 5,073,488. These indicators employ an enzyme whose activity is correlated with the growth of selected test microorganisms that are commonly used to monitor the effectiveness of a sterilization procedure, or "cycle". If the sterilization cycle creates a condition that is sufficient to kill the test microorganisms, the enzyme will be inactivated and there will be no detectable change in the biological indicator after the cycle is complete. However, if the sterilization cycle fails to create a condition that is sufficient to kill the test microorganisms, the enzyme will remain active and will react with a substrate in the biological indicator to form an enzyme-modified product. The enzyme-modified product then emits a detectable signal, either by itself or as a result of a further reaction with an additional compound. The detectable signal may be luminescence, fluorescence, or a color change.

The theory underlying the operation of enzyme indicators is that the enzyme inactivation will correlate with the death of test microorganisms. The enzyme selected for use in a biological indicator must therefore be at least as resistant to sterilization as the contaminating microorganisms, and preferably more resistant. The enzyme must remain sufficiently active to form a detectable enzyme-substrate product after a sterilization cycle that fails to kill contaminating microorganisms, yet must be inactivated by an effective sterilization cycle.

Enzymes used in enzyme biological indicators include enzymes derived from spore-forming microorganisms, which, themselves, are often used as biological indicators of the effectiveness of sterilization procedures. Dual biological indicators measure both enzyme activity and the growth of a test microorganism from which it is obtained, to monitor the effectiveness of a sterilization cycle. For example, the 3M™ Attest™ 1291 and 1292 Rapid Readout Biological Indicators measure the activity of the enzyme alpha-D-glucosidase, from *Bacillus stearothermophilus*, and the growth of *B. stearothermophilus* live spores. The 3M™ Attest™ Rapid Readout Biological Indicators are used to test the effectiveness of sterilization cycles.

Enzymes from spore-forming microorganisms that are useful as biological indicators include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-B-glucosaminodase, beta-D-cellobiosidase, alanine aminopeptidase, proline aminopeptidase and a fatty acid esterase, derived from spore forming microorganisms.

Chromogenic and fluorogenic substrates that react with enzymes to form detectable products are well known in the art. (M. Roth, *Methods of Biochemical Analysis*, Vol. 17, D. Block, Ed., Interscience Publishers, New York, 1969, p. 89; S. Udenfriend, *Fluorescence Assay in Biology and Medicine*, Academic Press, New York, 1962, p. 312; D. J. R. Lawrence, *Fluorescence Techniques for the Enzymologist*, Methods in Enzymology, Vol. 4, S. P. Colowick and N. O. Kaplan, Eds., Academic Press, New York, 1957, p. 174, incorporated herein by reference). These substrates create a visually detectable signal in one of two ways. The substrates in one group react with enzymes to form enzyme-modified products that are chromogenic or fluorescent. The substrates in the second group form enzyme-modified products that must react further with an additional compound to generate a color or fluorescent signal.

Typically the enzyme and substrate in a biological indicator are physically separated from each other during the sterilization procedure and then united afterwards. This is accomplished by employing a container having nesting outer and inner tubes. The outer tube is made of a compressible plastic and contains a sealed, glass inner tube which holds the substrate in a buffered aqueous solution. The enzyme is contained on a piece of filter paper or other appropriate carrier located in the space between the outer and inner tubes. The outer tube has a cap with at least one opening to allow sterilant to enter the outer tube and contact the enzyme during the sterilization cycle. After the sterilization cycle, the sides of the outer tube are compressed, breaking the inner tube and bringing the enzyme and substrate into contact with each other for the first time. The biological indicator is then incubated for a period of time sufficient for a fluorescent or colored product to be formed.

Microorganisms suited to function as biological indicators, either alone or as part of a dual indicator system, include *Bacillus stearothermophilus* and *Bacillus subtilis*. *Bacillus stearothermophilus* is particularly suited for monitoring steam sterilization procedures, and *Bacillus subtilis* is particularly suited for monitoring ethylene oxide sterilization. The microorganisms and the growth medium in the biological indicator are physically separated from each other during the sterilization cycle.

In a preferred embodiment of the invention, the biological indicator is a dual indicator that measures both enzyme activity and spore growth. The spores and enzyme may both be present on the same carrier material, and in fact the spores themselves may provide the source of enzyme for the indicator. In use, after the biological indicator has been exposed to the sterilization cycle, the strip containing the spores and enzyme is exposed to spore growth medium and substrate, then incubated. The enzyme substrate reaction occurs within a few hours and provides a rapid indication of cycle failure. Spore outgrowth takes up to seven days. A pH indicator in the growth medium changes color in response to spore growth. In the most preferred embodiment of the invention, both the substrate and spore growth medium are contained in the same sealed, inner container.

The protective housing of the present invention is designed to contain a biological indicator. When enzyme indicators are used, the housing prevents condensed sterilant from contacting and inactivating the enzyme, yet allows noncondensed sterilant to enter the housing and contact the enzyme during the sterilization procedure. When the biological indicator employs a live microorganism, either alone or as part of a dual system, the housing prevents the sterilant from interfering with the microorganism, as well. In the preferred embodiment, the protective housing is re-usable.

Figure 1:
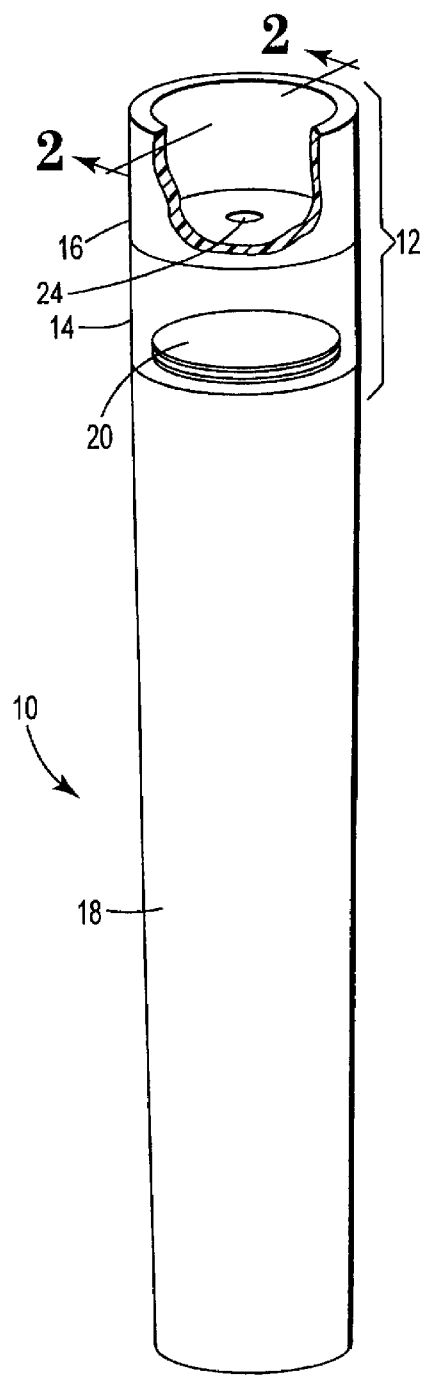
FIG. 1 is a perspective view of a preferred embodiment of a protective housing of the present invention, with a portion of the cap assembly cut away to show the sterilant access port.
Figure 2:
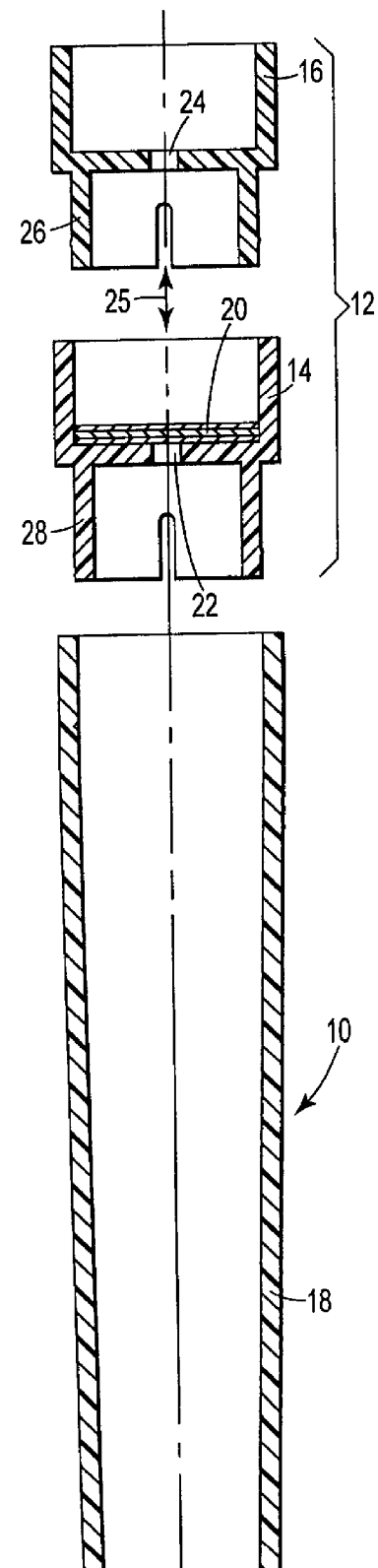
FIG. 2 is an exploded cross-sectional view of a preferred embodiment of a protective housing of the present invention.

Referring now to FIGS. 1 and 2, a protective housing 10 is illustrated having a housing tube 18 and a cap assembly 12. The cap assembly 12 preferably includes a first part 14 and a second part 16 that are adapted to couple with each other. The first part 14 is also adapted to couple with the open end of the housing tube 18. Sterilant access ports 22 and 24 in the cap assembly 12 create a channel 25 through which sterilant may enter housing tube 18 from the sterilization chamber and contact the biological indicator. During a sterilization cycle, sterilant enters the housing 10 through sterilant access port 22. Absorbent material 20, located in first cap part 14 of the cap assembly 12, absorbs any condensed sterilant and prevents it from passing though sterilant access port 22 and entering the housing tube 18. Noncondensed sterilant then enters tube 18 through sterilant port 22 and sterilizes the contents. The depth of the first cap portion 14 may be modified to accommodate the number of layers and thickness of absorbent material 20. The preferred depth is 9 mm. The lower flange 26 of second cap portion 16 may be sized in length so as to come in contact with absorbent material 20 in the recessed portion of first cap portion 14. The contact between flange 26 and absorbent material 20 secures the absorbent material 20 during the sterilization cycle.

The housing tube 18 must be made of a material which will withstand the high temperatures, vacuum and pressure changes commonly employed in sterilization processes. Conventional steam sterilizers generally reach temperatures on the order of 121° C.–135° C., and cycles may include multiple vacuum draws followed by steam injection. In addition, the walls of housing tube 18 must be substantially impermeable to gases and liquids, and substantially nonabsorptive of the particular sterilant being used in the sterilization procedure being monitored. Suitable materials for housing tube 18 include polycarbonate, polypropylene, polyamides, polymethylpentenes, various polyesters, polysulfone, polyethylene, polystyrene, teflon, glass and acrylics. Those of ordinary skill in the art will understand that selection of the appropriate material for housing tube 18 will depend on which sterilization procedure is being used. For steam sterilization procedures, suitable materials for housing tube 18 include polycarbonate, polypropylene, polyamides, polymethylpentenes, glass and polysulfone. For other sterilization procedures, such as ethylene oxide gas, hydrogen peroxide plasma, vapor phase hydrogen peroxide, and peracetic acid, materials with low sterilant residuals such as polyethylene, polypropylene, polystyrene, teflon, glass and acrylics should be used.

Housing tube 18 may be made by injection molding or extrusion. The housing tube 18 preferably is between about 70 mm to about 100 mm in length, has an inside diameter of about 12.7 mm to about 20.3 mm, and has a wall thickness of about 1.27 mm to about 3.81 mm. However, the size of the container will depend on several factors, including the type of sterilization process being used, the size of the biological indicator, and the required resistance criteria. The size of the housing may therefore be varied without deviating from the invention.

The cap assembly 12 may be made of the same material as the housing tube. In a preferred embodiment of the invention, friction fittings couple the first cap portion 14 to the second cap portion 16 and to the housing tube 18. In another embodiment, illustrated in FIGS. 8 and 9, threaded fittings couple the first cap portion 14 to the second cap portion 16 and to the housing tube 18. Other embodiments are possible without deviating from the invention. For example, in one alternative embodiment, threaded fittings may be used to couple the first and second cap portions to each other while friction fittings are used to join the cap assembly to the housing tube 18. And in yet another alternative embodiment, friction fittings may be used to couple the first and second cap portions to each other while threaded fittings are used to join the cap assembly 12 to the housing tube 18. However, this is not an exhaustive list of combinations. Any means for coupling pieces of plastic tubing together may be used, and all are within the invention.

In a preferred embodiment of the invention, tape is wrapped around the circumference of the protective housing before sterilization, over the seam between the first cap portion 14 and the second cap portion 16 of the cap assembly 12, and over the seam between the first cap portion 14 and the housing tube 18. Suitable tapes for this use include any tapes capable of withstanding the extreme temperatures and pressures of sterilization procedures without losing their adhesive properties. In a preferred embodiment of the invention, the tape used to wrap the protective housing may be any film-based label stock, such as ScotchMark™ 7880 Polyester Film Label. In the most preferred embodiment of the invention, the tape is a tape made especially for use in sterilizers. Sterilizer tapes suitable for use in the invention are described in U.S. Pat. No. 5,518,763 and 5,460,880, which are incorporated in their entirety herein by reference, 3M™ 1222 Autoclave Tape (available from 3M Company, St. Paul, Minn.) is a sterilizer tape that is suitable for use with the invention.

The sterilant access ports 22 and 24 may include one or more apertures each. In a preferred embodiment, illustrated in FIGS. 1–2 and 6, sterilant access port 22 on the first cap portion 14 includes one aperture, and sterilant access port 24 in the second cap portion 16 includes one aperture. In an alternative preferred embodiment, illustrated in FIG. 7, each of the access ports 22 and 24 includes three apertures. However, it will be understood by one skilled in the art that the number of apertures may be varied without deviating from the invention. For example, one alternative embodiment includes two apertures in each cap portion. Another alternative embodiment includes one aperture in the first cap portion and two or more apertures in the second cap portion. Yet another alternative embodiment includes two or more apertures in the first cap portion and one aperture in the second cap portion. In a preferred embodiment of the invention, the size of the sterilant apertures has a diameter in the range of about 1.52 mm to 5.08 mm. In the most preferred embodiment, the diameter is about 2.29 mm.

The absorbent material 20 in cap assembly 12 may be any material that will absorb condensed sterilant yet allow uncondensed sterilant to pass through the sterilant access port and contact the biological indicator. Suitable absorbent materials include guar gum, gum tragacanth, locust bean gum, gum arabic, xanthan gum, karaya gum, Gum Accroides, Gum Pontianak, Ghatti gum, hydroxypropyl methylcellulose, compressed blown microfibers such as those described in U.S. Pat. No. 5,024,865; heat and moisture exchange (HME) media such as those described in U.S. Pat. No. 5,577,494, infiltrated with superabsorbent polymeric fibers or particles such as those described in U.S. Pat. Nos. 4,650,479; 4,755,178; and 4,985,298; and filter paper discs coated with solutions of sugars or sugar alcohols (e.g., trehalose, sorbitol, mannitol, maltose, soluble starch, mannose, lactose, nigerose, xylitol, inositol, and myo-inositol). In addition, multiple layers of filter paper (e.g., 5111-067, Monadnock Paper Mills Inc., Bennington, N.H.) may increase the resistance of the spores and the enzyme. For non-steam sterilization, a combination of layers of filter paper and the absorbent materials listed may be used.

In a preferred embodiment of the invention, absorbent material 20 may include a filter paper disc coated with alditols; monosaccharides, disaccharides, trisaccharides, and tetrasaccharides; polymeric alcohols selected from polyvinyl alcohol, glycols, and diols; starches, cyclodextrins, pectins, and gums. Suitable materials for coating paper discs for use in the protective housing of the invention include D(+)-cellobiose, meso-inositol, xylitol, trehalose, adonitol, polyethylene glycol, dulcitol, D-mannitol, sucrose, myo-erythitol, and D-sorbitol. The coating weight of material on the paper discs is preferably about $1\times10^{-1}$ to $1\times10^{-7}$ g/mm2, more preferably about $1\times10^{-4}$ to $1\times10^{-6}$ g/mm2, and most preferably about $9\times10^{-5}$ to $1\times10{-5}$ g/mm2. The preferred filter paper for this use is 5111-067, available from Monadnock Mills Inc., Bennington, N.H.

In a more preferred embodiment of the invention, the absorbent material 20 is an absorbent gum material. Absorbent gums that are suitable for use in the invention include guar gum, gum tragacanth, locust bean gum, gum arabic, xanthan gum, karaya gum, Gum Accroides, Gum Pontianak, and Ghatti gum. In the most preferred embodiment of the invention, the absorbent material is Ghatti gum, a gummy exudate from the stems of *Anogeissus latifolia* Ghatti gum is a complex water-soluble polysaccharide occurring as a calcium-magnesium salt; composed of L-arabinose, D-galactose, D-mannose, D-xylose, D-glucuronic acid, in a molar ratio of 10:6:2:1:2, and traces of D-6-deoxyhexose. *The Merck Index* ($12^{th}$ Edition 1996). In the most preferred embodiment, 0.09 g Ghatti Gum is placed in the first cap portion 14 of the cap assembly 12. In the most preferred embodiment, Ghatti gum is sandwiched between layers of filter paper and placed in the first cap portion 14. The preferred filter paper for this use is 5111-067, available from Monadnock Mills Inc., Bennington, N.H. Other absorbent materials may also be used in the invention. An alternative embodiment uses multiple layers of filter paper or other absorbent sheeting material as absorbent material 20.

One measure of the absorbency of a material is the ratio of its particle diameter in water to its particle diameter in acetone (water-acetone ratio). Many highly absorbent materials have higher water-acetone ratios than materials that are less absorbent or nonabsorbent. Ghatti gum is highly absorbent and has a water-acetone ratio of 15. In one embodiment of the invention, the absorbent material comprises a material with an absorbency such that the ratio of its particle diameter in water to its particle diameter in acetone is at least about 1.

In addition to the protective housing, the present invention also includes a sterilization monitor assembly, which is illustrated in FIG. 3–4. The sterilization monitor assembly 30 includes protective housing 10 and a biological indicator 32 within the protective housing 10. The biological indicator 32 may be of any type known to be useful for testing the effectiveness of a sterilization cycle. In a preferred embodiment, the biological indicator includes live microorganisms and a means for generating a detectable signal if the microorganisms survive the sterilization procedure. In a more preferred embodiment, the biological indicator includes an enzyme whose activity is correlated with the survival of test microorganisms commonly used to monitor sterilization, and a substrate. If the sterilization cycle fails, the enzyme remains active and reacts with a substrate to form a detectable enzyme-substrate product. In another preferred embodiment, the biological indicator is a dual indicator which includes both an enzyme indicator and live spores.

In a preferred embodiment of the sterilization monitor assembly, the biological indicator is a live microorganism that is more resistant to sterilization than contaminating microorganisms. As illustrated in FIG. 5, the biological indicator 32 includes nesting containers that separate the various components of the system from each other until after the sterilization cycle is complete. The biological indicator 32 includes an outer tube 36, a sealed inner tube 34 and a vented cap 42. Outer tube 36 is made of a compressible plastic. Inner tube 34 is made of glass or some other frangible material. Preferably the biological indicator 32 is upside down relative to the protective housing 10. During a sterilization cycle, sterilant enters the outer tube 36 through vent 44 in the vented cap 42 and contacts microorganism spores on carrier material 38. The sterilant does not contact the contents of sealed inner tube 34, however. Sealed inner tube 34 contains spore growth medium having a pH indicator that changes color if spores grow. After the sterilization procedure is complete, the inner tube is broken and the microorganism spores are mixed with the growth medium and incubated. A color change indicates that spores have survived and the sterilization cycle has failed.

In a more preferred embodiment of the sterilization monitor assembly, the biological indicator is an enzyme that is inactivated by a sterilization procedure that is sufficient to kill a test microorganism commonly used to monitor sterilization, and that retains its activity after exposure to a sterilization procedure that is sublethal to the test microorganism. The enzyme is retained on carrier 38. Sealed inner tube 34 contains a substrate solution that reacts with active enzyme to form a detectable enzyme-substrate product if the sterilization cycle fails. Chromogenic and fluorogenic substrates are known in the art that emit visible signals upon reaction with substrates. During a sterilization cycle, the sterilant contacts the enzyme on carrier 38 but does not contact the substrate solution in sealed inner tube 34. After the cycle is complete, the inner tube 34 is broken and the enzyme is mixed with the substrate and incubated. A visible reaction indicates that enzyme has survived and the sterilization cycle has failed.

In an alternative preferred embodiment of the sterilization monitor assembly, the biological indicator is a dual indicator that includes both a live microorganism indicator and an enzyme indicator. The carrier 38 in this embodiment has both microorganism spores and active enzyme impregnated upon its surface. In the most preferred embodiment, the spores are the source of active enzyme. The inner tube 34 contains spore growth medium and enzyme substrate. After the sterilization cycle is complete, the inner tube 34 is broken, and the carrier strip is exposed to its contents and incubated. The enzyme test produces visible results within a few hours, and the live microorganism growth test confirms these results within seven days. The 3M™ Attest™ Rapid Readout Biological Indicator is a dual indicator that uses both a live microorganism and an enzyme-substrate system. With the Attest™ indicators, if the sterilization cycle fails, the enzyme alpha-glucosidase reacts with the substrate 4-methylumbelliferyl-alpha-D-glucoside within 3 hours to produce a fluorescent signal. The Attest™ indicators also contain a viable population of *Bacillus stearothermophilus* spores that grow and create a color change in the growth medium in the event of cycle failure.

Figure 10:
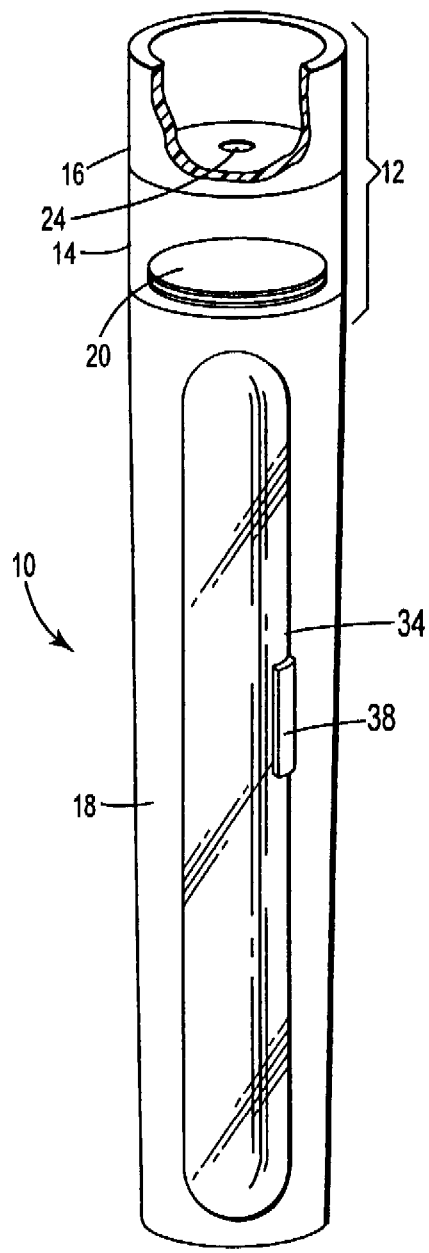
FIG. 10 is a perspective view of an embodiment of the sterilization monitor assembly of the invention.

In another embodiment of the sterilization monitor assembly, illustrated in FIG. 10, protective housing 10 contains sealed inner tube 34 and carrier material 38, upon which is impregnated microorganisms, enzymes or both. Sealed inner tube 34 contains microorganism growth medium, enzyme substrate or both. After the sterilization procedure the wall of housing tube 18 is compressed, breaking the inner tube 34 and allowing its contents to contact carrier material 38. As discussed above, failure of the sterilization procedure is indicated by fluorescence in the case of enzyme indicators or a color change from outgrowth of microorganism spores.

The invention also includes a method for testing the effectiveness of a sterilization procedure. In the method of the invention, referring again to FIGS. 3 and 4, the sterilization monitor assembly 30 of the invention is subjected to a sterilization procedure, which may be any commonly used procedure including procedures that use steam, dry heat, gas, hydrogen peroxide vapor phase, hydrogen peroxide plasma phase, ethylene oxide, propylene oxide, methyl bromide, chlorine dioxide, formaldehyde, peracetic acid (alone or with a plasma phase), and any other gaseous or liquid agents. In the preferred embodiment, the sterilization procedure uses steam as a sterilant. In the most preferred embodiment, the sterilization procedure is a pre-vacuum sterilization procedure in which a vacuum is drawn in the sterilization chamber before steam is introduced. During the sterilization process, sterilant enters the protective housing 10 through sterilant access port 24. Absorbent material 20 absorbs any sterilant that condenses, and noncondensed sterilant passes through sterilant access port 22 into the housing tube 18. The sterilant enters the biological indicator 32 through vent 44 of cap 42 and contacts the biological specimen, either microorganisms or enzymes or both, on carrier 38. After the sterilization procedure is complete the biological specimen on carrier 38 is exposed to the contents of the inner tube 34, either growth medium or substrate or both, and incubated. Following incubation, the biological indicator is examined for a fluorescent or color change indicating that the sterilization has failed to kill or inactivate the biological specimen on carrier 38.

EXAMPLE 1

Comparison of Biological Indicator Performance with and without Protective Housing in 121° C. (250° F.) Prevacuum Sterilization Cycle The accuracy of Attest™ 1292 Rapid Biological Indicator with and without protective housings was compared in a 121° C. (250° F.) pre-vacuum sterilization procedure. Separate groups of tubes were exposed to sterilization for 5 min, 7 min, 9 min, 11 min, 13 min and 15 min. For each exposure period, ten tubes were tested with protective housings and ten tubes were tested without protective housings.

The protective housings for the biological indicators contained 0.09 g Ghatti gum between 2 layers of filter paper (Monadnock Paper Mills, Inc., Bennington, N.H., 5111-067) in the lower cap of a double-cap assembly. The cap assembly was sealed with 3M Autoclave tape.

Tubes were subjected to sterilization in a Getinge sterilizer using a 121° C. pre-vacuum cycle: vacuum $7.5 \times 10^3$ Pa (0.075 bar); steam $2 \times 10^5$ Pa (2.000 bar). The sterilization monitor assemblies were then disassembled and the biological indicators incubated at 60° C. The sterilization monitor assemblies were examined for fluorescence from enzymes at 3 and 4 hours, and for color change indicating spore outgrowth at 24, 48 and 168 hours.

Table 1 records the number of tubes positive for fluorescence and spore growth per 10 tubes tested for each exposure time, at each observation time. In the table, "Attest™" refers to the biological indicators exposed without protective housings, and "Test" refers to biological indicators exposed in protective housings. The accuracy of the enzyme indicator is measured by comparing the number of growth positives at 168 hours with the number of fluorescent positives at 3 hours and 4 hours. Table 1 shows that use of the protective housing reduces false negatives and improves accuracy.

TABLE 1

| Tube | Exposure Time (min) | Fluorescent Positives/10 tubes tested | | Spore Outgrowth Positives/10 tubes tested | | |
|---|---|---|---|---|---|---|
| | | 3 hr | 4 hr | 24 hr | 48 hr | 168 hr |
| Attest ™ | 5:00 | 10 | 10 | 10 | 10 | 10 |
| Test | | 10 | 10 | 10 | 10 | 10 |
| Attest ™ | 7:00 | 6 | 8 | 9 | 9 | 9 |
| Test | | 10 | 10 | 10 | 10 | 10 |
| Attest ™ | 9:00 | 0 | 0 | 9 | 9 | 9 |
| Test | | 3 | 3 | 1 | 1 | 1 |
| Attest ™ | 11:00 | 0 | 0 | 1 | 1 | 1 |
| Test | | 1 | 1 | 1 | 1 | 1 |
| Attest ™ | 13:00 | 0 | 0 | 1 | 1 | 1 |
| Test | | 1 | 1 | 0 | 0 | 0 |
| Attest ™ | 15:00 | 0 | 0 | 0 | 0 | 0 |
| Test | | 0 | 0 | 0 | 0 | 0 |

EXAMPLE 2

Absorptivity of Materials

The absorptivities of various absorptive materials useful in the protective housing of the invention were measured and are recorded in Table 5. Samples of Ghatti gum, Guar gum, locust bean gum and hydroxypropyl methylcellulose were placed in glass test tubes with an excess of water or acetone. The particle diameters were measured in acetone and water using a Coulter™ LS Particle Size Analyser. The particle diameter in acetone gives an indication of the size of the particles prior to swelling. The particle diameter in water gives an indication of the ability of the materials to swell to absorb liquids, such as condensed sterilant during a sterilization procedure.

Of the materials tested, Ghatti gum has the smallest unswollen particle diameter in acetone (22.64 micrometers), yet increased its size in contact with water to 348 micrometers, which is much larger than the particle size of the other materials tested. The ratio of swollen and unswollen particle diameters for Ghatti gum is 15, several times any of the others. The initial small size of the Ghatti gum particles would give a large surface area per unit mass to act as an absorptive surface compared to the other materials tested.

TABLE 2

| Material | Particle Diameter In Acetone (micrometers) | Particle Diameter In Water (micrometers) | Ratio of Particle Diameters Water/Acetone |
|---|---|---|---|
| Ghatti Gum | 22.64 | 348 | 15 |
| Guar Gum | 85.69 | 149 | 1.7 |
| Locust Bean Gum | 206.5 | 246.2 | 1.2 |
| Methylcellulose (HPMC) | 126.3 | 81.7 | 0.65 |

EXAMPLE 3

Coated Paper Discs as Absorptive Material in Protective Housing

The absorptive effectiveness of paper discs coated with several different coating materials were compared to each other and to uncoated paper discs in the protective housing of the invention. The coating materials tested included D(+)-cellobiose, meso-inositol, xylitol, trehalose, adonitol, polyethylene glycol, dulcitol, D-mannitol, sucrose, myo-erythritol, and D-sorbitol. Paper discs of 5111-067 filter paper from Monadnock Paper Mills, Inc., having a 127 mm diameter were coated with the percent concentrations (w/v) specified in Table 6 to obtain coating weights of approximately $3.0 \times 10^{-5}$ g/mm$^2$. 50 ul of solution was pipetted onto each of the paper discs and allowed to dry under ambient conditions for 48 hours.

Sterilization monitor assemblies according to the invention were assembled using the coated paper discs as absorptive material and Attest™ 1292 biological indicators. For each coating material and concentration of coating material tested, three sterilization monitor assemblies were prepared and simultaneously exposed to 5, 6, 7, 8, 9, 10, 11, and 12 minutes to a 121° C. prevacuum steam sterilization cycle: vacuum $7.5 \times 10^3$ Pa (0.075 bar); steam $2 \times 10^5$ Pa (2.000 bar), in a Getinge sterilizer. After exposure the sterilization monitor assemblies were disassembled and the biological indicators were incubated at 60° C. Fluorescent readout was recorded at 3 hours, and color change indicating spore outgrowth was recorded at 24, 48 and 168 hours.

Table 6 the number of tubes positive for fluorescence and spore growth per 3 tubes tested for each exposure time, at each observation time. The accuracy of the enzyme indicator is measured by comparing the number of growth positive at 168 hours with the number of fluorescent positives at 3 hours. This example illustrates that paper discs coated with alditols and polymeric alcohols are effective when used as the absorbent material of the invention, and reduce false negatives when compared to uncoated paper discs.

TABLE 3

121° C. Prevacuum Exposure - Number Positive/3 Units Tested

| Absorbent Coating (w/v) | Exposure Time (min.) | Fluorescence 3 hr | Spore Outgrowth 24 hr | Spore Outgrowth 48 hr | Spore Outgrowth 168 hr |
|---|---|---|---|---|---|
| uncoated | 5 | 3 | 3 | 3 | 3 |
|  | 6 | 3 | 3 | 3 | 3 |
|  | 7 | 3 | 3 | 3 | 3 |
|  | 8 | 0 | 3 | 3 | 3 |
|  | 9 | 0 | 3 | 3 | 3 |
|  | 10 | 0 | 2 | 2 | 2 |
|  | 11 | 0 | 1 | 1 | 1 |
|  | 12 | 0 | 0 | 0 | 0 |
| cellobiose (20%) | 5 | 3 | 3 | 3 | 3 |
|  | 6 | 3 | 3 | 3 | 3 |
|  | 7 | 3 | 3 | 3 | 3 |
|  | 8 | 3 | 3 | 3 | 3 |
|  | 9 | 0 | 0 | 0 | 0 |
|  | 10 | 0 | 0 | 0 | 0 |
|  | 11 | 0 | 0 | 0 | 0 |
|  | 12 | 0 | 0 | 0 | 0 |
| cellobiose (30%) | 5 | 3 | 3 | 3 | 3 |
|  | 6 | 3 | 3 | 3 | 3 |
|  | 7 | 3 | 3 | 3 | 3 |
|  | 8 | 3 | 3 | 3 | 3 |
|  | 9 | 0 | 0 | 0 | 0 |
|  | 10 | 0 | 0 | 0 | 0 |
|  | 11 | 0 | 0 | 0 | 0 |
|  | 12 | 0 | 0 | 0 | 0 |
| meso-inositol (10%) | 5 | 3 | 3 | 3 | 3 |
|  | 6 | 3 | 3 | 3 | 3 |
|  | 7 | 3 | 3 | 3 | 3 |
|  | 8 | 3 | 0 | 0 | 0 |
|  | 9 | 1 | 1 | 1 | 1 |
|  | 10 | 0 | 0 | 0 | 0 |
|  | 11 | 0 | 0 | 0 | 0 |
|  | 12 | 0 | 0 | 0 | 0 |
| meso-inositol (20%) | 5 | 3 | 3 | 3 | 3 |
|  | 6 | 3 | 3 | 3 | 3 |
|  | 7 | 3 | 3 | 3 | 3 |
|  | 8 | 3 | 0 | 0 | 0 |
|  | 9 | 2 | 1 | 1 | 1 |
|  | 10 | 0 | 0 | 0 | 0 |
|  | 11 | 0 | 0 | 0 | 0 |
|  | 12 | 0 | 0 | 0 | 0 |
| xylitol (20%) | 5 | 3 | 3 | 3 | 3 |
|  | 6 | 3 | 3 | 3 | 3 |
|  | 7 | 3 | 3 | 3 | 3 |
|  | 8 | 0 | 0 | 0 | 0 |
|  | 9 | 3 | 0 | 0 | 0 |
|  | 10 | 0 | 0 | 0 | 0 |
|  | 11 | 0 | 0 | 0 | 0 |
|  | 12 | 0 | 0 | 0 | 0 |
| xylitol (30%) | 5 | 3 | 3 | 3 | 3 |
|  | 6 | 3 | 3 | 3 | 3 |
|  | 7 | 3 | 3 | 3 | 3 |
|  | 8 | 1 | 0 | 0 | 0 |
|  | 9 | 3 | 0 | 0 | 0 |
|  | 10 | 0 | 0 | 0 | 0 |
|  | 11 | 0 | 0 | 0 | 0 |
|  | 12 | 0 | 0 | 0 | 0 |
| trehalose 10% | 5 | 3 | 3 | 3 | 3 |
|  | 6 | 3 | 3 | 3 | 3 |
|  | 7 | 3 | 3 | 3 | 3 |
|  | 8 | 3 | 1 | 1 | 1 |
|  | 9 | 3 | 0 | 0 | 0 |
|  | 10 | 0 | 0 | 0 | 0 |
|  | 11 | 0 | 0 | 0 | 0 |
|  | 12 | 0 | 0 | 0 | 0 |
| trehalose (20%) | 5 | 3 | 3 | 3 | 3 |
|  | 6 | 3 | 3 | 3 | 3 |
|  | 7 | 3 | 3 | 3 | 3 |
|  | 8 | 3 | 0 | 0 | 0 |
|  | 9 | 3 | 0 | 0 | 0 |
|  | 10 | 0 | 0 | 0 | 0 |
|  | 11 | 0 | 0 | 0 | 0 |
|  | 12 | 0 | 0 | 0 | 0 |
| adonitol (10%) | 5 | 3 | 3 | 3 | 3 |
|  | 6 | 3 | 3 | 3 | 3 |
|  | 7 | 3 | 3 | 3 | 3 |
|  | 8 | 3 | 2 | 2 | 2 |
|  | 9 | 3 | 0 | 0 | 0 |
|  | 10 | 0 | 0 | 0 | 0 |
|  | 11 | 0 | 0 | 0 | 0 |
|  | 12 | 0 | 0 | 0 | 0 |
| adonitol (20%) | 5 | 3 | 3 | 3 | 3 |
|  | 6 | 3 | 3 | 3 | 3 |
|  | 7 | 3 | 3 | 3 | 3 |
|  | 8 | 3 | 3 | 3 | 3 |
|  | 9 | 2 | 0 | 0 | 0 |
|  | 10 | 0 | 0 | 0 | 0 |
|  | 11 | 0 | 0 | 0 | 0 |
|  | 12 | 0 | 0 | 0 | 0 |
| polyethylene glycol (10%) | 5 | 3 | 3 | 3 | 3 |
|  | 6 | 3 | 3 | 3 | 3 |
|  | 7 | 3 | 3 | 3 | 3 |
|  | 8 | 3 | 3 | 3 | 3 |
|  | 9 | 3 | 2 | 2 | 2 |
|  | 10 | 3 | 0 | 0 | 0 |
|  | 11 | 0 | 0 | 0 | 0 |
|  | 12 | 0 | 0 | 0 | 0 |
| polyethylene glycol (20%) | 5 | 3 | 3 | 3 | 3 |
|  | 6 | 3 | 3 | 3 | 3 |
|  | 7 | 3 | 3 | 3 | 3 |
|  | 8 | 3 | 3 | 3 | 3 |
|  | 9 | 3 | 2 | 2 | 2 |
|  | 10 | 3 | 0 | 0 | 0 |
|  | 11 | 0 | 0 | 0 | 0 |
|  | 12 | 0 | 0 | 0 | 0 |

TABLE 3-continued

121° C. Prevacuum Exposure - Number Positive/3 Units Tested

| Absorbent Coating (w/v) | Exposure Time (min.) | Fluorescence 3 hr | Spore Outgrowth 24 hr | Spore Outgrowth 48 hr | Spore Outgrowth 168 hr |
|---|---|---|---|---|---|
| ducitol (10%) | 5 | 3 | 3 | 3 | 3 |
| | 6 | 3 | 3 | 3 | 3 |
| | 7 | 3 | 3 | 3 | 3 |
| | 8 | 3 | 3 | 3 | 3 |
| | 9 | 3 | 2 | 2 | 2 |
| | 10 | 0 | 0 | 0 | 0 |
| | 11 | 0 | 0 | 0 | 0 |
| | 12 | 0 | 0 | 0 | 0 |
| mannitol 10% | 5 | 3 | 3 | 3 | 3 |
| | 6 | 3 | 3 | 3 | 3 |
| | 7 | 3 | 3 | 3 | 3 |
| | 8 | 3 | 3 | 3 | 3 |
| | 9 | 0 | 0 | 0 | 0 |
| | 10 | 0 | 0 | 0 | 0 |
| | 11 | 0 | 0 | 0 | 0 |
| | 12 | 0 | 0 | 0 | 0 |
| mannitol (20%) | 5 | 3 | 3 | 3 | 3 |
| | 6 | 3 | 3 | 3 | 3 |
| | 7 | 3 | 3 | 3 | 3 |
| | 8 | 3 | 3 | 3 | 3 |
| | 9 | 0 | 0 | 0 | 0 |
| | 10 | 0 | 0 | 0 | 0 |
| | 11 | 0 | 0 | 0 | 0 |
| | 12 | 0 | 0 | 0 | 0 |
| sucrose (20%) | 5 | 3 | 3 | 3 | 3 |
| | 6 | 3 | 3 | 3 | 3 |
| | 7 | 3 | 3 | 3 | 3 |
| | 8 | 3 | 3 | 3 | 3 |
| | 9 | 3 | 2 | 2 | 2 |
| | 10 | 0 | 0 | 0 | 0 |
| | 11 | 0 | 0 | 0 | 0 |
| | 12 | 0 | 0 | 0 | 0 |
| sucrose (30%) | 5 | 3 | 3 | 3 | 3 |
| | 6 | 3 | 3 | 3 | 3 |
| | 7 | 3 | 3 | 3 | 3 |
| | 8 | 3 | 3 | 3 | 3 |
| | 9 | 2 | 0 | 0 | 0 |
| | 10 | 0 | 0 | 0 | 0 |
| | 11 | 0 | 0 | 0 | 0 |
| | 12 | 0 | 0 | 0 | 0 |
| myo-erythitol (10%) | 5 | 3 | 3 | 3 | 3 |
| | 6 | 3 | 3 | 3 | 3 |
| | 7 | 3 | 3 | 3 | 3 |
| | 8 | 3 | 3 | 3 | 3 |
| | 9 | 2 | 0 | 0 | 0 |
| | 10 | 0 | 0 | 0 | 0 |
| | 11 | 0 | 0 | 0 | 0 |
| | 12 | 0 | 0 | 0 | 0 |
| myo-erythitol (20%) | 5 | 3 | 3 | 3 | 3 |
| | 6 | 3 | 3 | 3 | 3 |
| | 7 | 3 | 3 | 3 | 3 |
| | 8 | 3 | 3 | 3 | 3 |
| | 9 | 3 | 0 | 0 | 0 |
| | 10 | 2 | 0 | 0 | 0 |
| | 11 | 0 | 0 | 0 | 0 |
| | 12 | 0 | 0 | 0 | 0 |
| D-sorbitol (40%) | 5 | 3 | 3 | 3 | 3 |
| | 6 | 3 | 3 | 3 | 3 |
| | 7 | 3 | 3 | 3 | 3 |
| | 8 | 3 | 3 | 3 | 3 |
| | 9 | 3 | 0 | 0 | 0 |
| | 10 | 0 | 0 | 0 | 0 |
| | 11 | 0 | 0 | 0 | 0 |
| | 12 | 0 | 0 | 0 | 0 |

What is claimed is:

1. A protective housing for a biological indicator for testing the effectiveness of a sterilization procedure, said protective housing comprising:

(a) a tube having an open end and a closed end, said tube being constructed of a material that is substantially liquid impermeable and substantially gas nonabsorptive;

(b) a cap assembly for mounting on said tube, said cap assembly having a sterilant access port therethrough to allow sterilant to enter said housing;

(c) an absorbent material in said cap assembly to substantially restrict access of condensed sterilant to said biological indicator.

2. A protective housing according to claim 1, wherein the cap assembly includes a first cap portion and a second cap portion, said first cap portion being adapted at one end to couple with said open end of said tube and adapted at the other end to couple with said second cap portion.

3. A protective housing according to claim 2, wherein friction fittings couple the portions of the cap assembly to each other and couple the cap assembly to and the tube.

4. A protective housing according to claim 2, wherein threaded fittings couple the portions of the cap assembly to each other and couple the cap assembly to the tube.

5. A protective housing according to claim 2, wherein said absorbent material is in the first cap portion.

6. A protective housing according to claim 1, wherein said absorbent material comprises an absorbent gum material.

7. A protective housing according to claim 1, wherein said absorbent material is selected from the group consisting of guar gum, gum tragacanth, locust bean gum, gum arabic, xanthan gum, karaya gum, Gum Accroides, Gum Pontianak, and Ghatti gum, and mixtures of two or more materials in the group.

8. A protective housing according to claim 1, wherein said absorbent material is Ghatti gum.

9. A protective housing according to claim 1, wherein the absorbent material comprises particles with an absorbency such that the ratio of its particle diameter in water to its particle diameter in acetone is at least about 1.

10. A protective housing according to claim 1, wherein said absorbent material is a paper disc coated with a material selected from the group consisting of: D(+)-cellobiose, meso-inositol, xylitol, trehalose, adonitol, polyethylene glycol, dulcitol, D-mannitol, sucrose, myo-erythritol, sorbitol, and mixtures of two or more materials in the group.

11. A protective housing according to claim 2, wherein said sterilant access port comprises a fluid passageway in the first and second portions of the cap assembly.

12. A protective housing according to claim 2, wherein said sterilant access port comprises a plurality of passageways through the first and second portions of the cap assembly.

13. A protective housing according to claim 1, wherein said absorbent material comprises a layer of absorbent gum between layers of filter paper.

14. A protective housing according to claim 1, wherein the sterilant used in the sterilization procedure is selected from the group consisting of steam, dry heat, gas, hydrogen peroxide vapor phase, hydrogen peroxide plasma phase, ethylene oxide gas, propylene oxide, methyl bromide, chlorine dioxide, formaldehyde, and peracetic acid (alone or with a plasma phase).

15. A protective housing according to claim 2, wherein the sterilization procedure comprises first drawing a vacuum in the sterilization chamber and then introducing steam.

16. A sterilization monitor assembly for testing the effectiveness of a sterilization procedure, said sterilization monitor assembly comprising:

(a) a protective housing for a biological indicator comprising:

(i) a tube having an open end and a closed end, said tube being constructed of a material that is substantially liquid impermeable and substantially gas nonabsorptive;

(ii) a cap assembly for mounting on said tube, said cap assembly having a sterilant access port therethrough to allow sterilant to enter said housing; and (iii) an absorbent material in said cap assembly to substantially restrict access of condensed sterilant to said biological indicator; and (b) a biological indicator that produces a detectable signal if a sterilization procedure fails to kill substantially all contaminating microorganisms.

17. A sterilization monitor assembly according to claim 16, wherein said cap assembly includes a first cap portion and a second cap portion, said first cap portion being adapted at one end to couple with the open end of said tube and adapted at the other end to couple with said second cap portion.

18. A sterilization monitor assembly according to claim 16, wherein said biological indicator comprises:

(a) an enzyme that is inactivated by a sterilization procedure that kills substantially all contaminating microorganisms;

(b) a substrate that reacts with active enzyme to form a detectable enzyme-modified product in the event that the sterilization procedure fails to kill substantially all contaminating microorganisms.

19. A sterilization monitor assembly according to claim 16, wherein the biological indicator comprises:

(a) a first inner tube constructed of compressible plastic having a cap that allows sterilant to enter the first inner tube;

(b) a second inner tube located within the first inner tube, said second inner tube constructed of frangible material that can be broken, by compressing the walls of the first inner tube, to allow the contents of the first and second inner tubes to be mixed together;

(c) an enzyme located between the walls of said first and second inner tubes that is inactivated by a sterilization procedure that kills substantially all contaminating microorganisms; and (d) a substrate within said second inner tube that reacts with said enzyme to form a detectable enzyme-modified product in the event that the sterilization procedure fails to kill substantially all contaminating microorganisms.

20. A sterilization monitor assembly according to claim 16, wherein the detectable signal from the biological indicator is luminescence, fluorescence, or a color change.

21. A sterilization monitor assembly according to claim 17, wherein the absorbent material is in the first cap portion of the cap assembly.

22. A sterilization monitor assembly according to claim 16, wherein the absorbent material comprises an absorbent gum.

23. A sterilization monitor assembly according to claim 16, wherein said absorbent material is selected from the group consisting of guar gum, gum tragacanth, locust bean gum, gum arabic, xanthan gum, karaya gum, Gum Accroides, Gum Pontianak, and Ghatti gum, and mixtures of two or more materials in the group.

24. A sterilization monitor assembly according to claim 16, wherein the absorbent material comprises Ghatti gum.

25. A sterilization monitor assembly according to claim 16, wherein the absorbent material comprises particles with an absorbency such that the ratio of its particle diameter is water to its particle diameter is acetone is at least about 1.

26. A sterilization monitor assembly according to claim 16, wherein the absorbent material is a paper disc coated with a material selected from the group including: D(+)-cellobiose, meso-inositol, xylitol, trehalose, adonitol, polyethylene glycol, dulcitol, D-mannitol, sucrose, myo-erythritol, and sorbitol, and mixtures of two or more materials in the group.

27. A sterilization monitor assembly according to claim 17, wherein friction fittings couple the portions of the cap assembly to each other and couple the cap assembly to the tube.

28. A sterilization monitor assembly according to claim 17, wherein threaded fittings couple the portions of the cap assembly to each other and couple the cap assembly to the tube.

29. A sterilization monitor assembly according to claim 17, wherein the sterilant access port comprises an aperture through the first and second portions of the cap assembly.

30. A sterilization monitor assembly according to claim 17, wherein the sterilant access port comprises a plurality of apertures through the first and second portions of the cap assembly.

31. A sterilization monitor assembly according to claim 17, wherein the sterilant used in the sterilization procedure is selected from the group consisting of: steam, dry heat, gas, hydrogen peroxide vapor phase, hydrogen peroxide plasma phase, ethylene oxide gas, propylene oxide, methyl bromide, chlorine dioxide, formaldehyde, and peracetic acid (alone or with a plasma phase).

32. A sterilization monitor assembly according to claim 16, wherein the sterilization procedure comprises first drawing a vacuum in the sterilization chamber and then introducing steam.

33. A method for testing the effectiveness of a sterilization procedure, comprising the steps of:

(a) providing a sterilization monitor assembly comprising:

(i) a protective housing for a biological indicator including:

a) a tube having an open end and a closed end, said tube being constructed of a material that is substantially liquid-impermeable and substantially gas nonabsorptive;

b) a cap assembly for mounting on said tube, said cap assembly having a sterilant access port therethrough to allow sterilant to enter said housing; and c) an absorbent material in said cap assembly to substantially restrict access of condensed sterilant to the interior of said housing; and (ii) a biological indicator that produces a detectable signal if a sterilization procedure fails to kill substantially all contaminating microorganisms;

(b) subjecting said sterilization monitor assembly to a sterilization procedure; and (c) examining said biological indicator for a detectable signal indicating that said sterilization procedure failed to kill substantially all contaminating microorganisms.

34. A method for testing the effectiveness of a sterilization procedure according to claim 33, wherein said cap assembly includes a first cap portion and a second cap portion, said first cap portion being adapted at one end to couple with the open end of said tube and adapted at the other end to couple with the second cap portion.

35. A method for testing the effectiveness of a sterilization procedure according to claim 33, wherein the biological indicator comprises:

(a) an enzyme that is inactivated by a sterilization procedure that kills substantially all contaminating microorganisms;

(b) a substrate that reacts with active enzyme to form a detectable enzyme-modified product in the event that the sterilization procedure fails to kill substantially all contaminating microorganisms.

36. A method for testing the effectiveness of a sterilization procedure according to claim 33, wherein the biological indicator comprises:

(a) a first inner tube constructed of compressible plastic having a cap that allows sterilant to enter the first inner tube;

(b) a second inner tube located within the first inner tube, said second inner tube being constructed of frangible material that can be broken after a sterilization procedure, by compressing the walls of the first inner tube, to allow the contents of the first and second inner tubes to be mixed together;

(c) an enzyme located between the walls of said first and second inner tubes that is inactivated by a sterilization procedure that kills substantially all contaminating microorganisms; and (d) a substrate within said second inner tube that reacts with said enzyme to form a detectable enzyme-modified product in the event that the sterilization procedure fails to kill substantially all contaminating microorganisms.

37. A method for testing the effectiveness of a sterilization procedure according to claim 33, wherein the sterilant used in the sterilization procedure is selected from the group consisting of steam, dry heat, gas, hydrogen peroxide vapor phase, hydrogen peroxide plasma phase, ethylene oxide gas, propylene oxide, methyl bromide, chlorine dioxide, formaldehyde, and peracetic acid (alone or with a plasma phase).

38. A method for testing the effectiveness of a sterilization procedure according to claim 33, wherein the sterilization procedure comprises first drawing a vacuum in the sterilization chamber and then introducing steam.

39. A method for testing the effectiveness of a sterilization procedure according to claim 33, wherein the detectable signal from the biological indicator is luminescence, fluorescence, or a color change.

40. A method for testing the effectiveness of a sterilization procedure according to claim 34, wherein said absorbent material is in the first cap portion said cap assembly.

41. A method for testing the effectiveness of a sterilization procedure according to claim 33, wherein said absorbent material comprises an absorbent gum.

42. A method for testing the effectiveness of a sterilization procedure according to claim 33, wherein said absorbent material is selected from the group consisting of guar gum, gum tragacanth, locust bean gum, gum arabic, xanthan gum, karaya gum, Gum Accroides, Gum Pontianak, and Ghatti gum, and mixtures of two or more materials in the group.

43. A method for testing the effectiveness of a sterilization procedure according to claim 33, wherein said absorbent material comprises Ghatti gum.

44. A method for testing the effectiveness of a sterilization procedure according to claim 33, wherein the absorbent material comprises particles with an absorbency such that the ratio of its particle diameter is water to its particle diameter is acetone is at least about 1.

45. A method for testing the effectiveness of a sterilization procedure according to claim 34, wherein friction fittings couple the portions of the cap assembly to each other and couple the cap assembly to the tube.

46. A method for testing the effectiveness of a sterilization procedure according to claim 34, wherein threaded fittings couple the portions of the cap assembly to each other and couple the cap assembly to the tube.

47. A method for testing the effectiveness of a sterilization procedure according to claim 34, wherein the sterilant access port comprises an aperture through the first and second portions of the cap assembly.

48. A method for testing the effectiveness of a sterilization procedure according to claim 34, wherein the sterilant access port comprises a plurality of apertures through the first and second portions of the cap assembly.

49. A protective cap assembly for a biological indicator comprising:

(a) a cap for mounting on a tube that contains a biological indicator for testing the effectiveness of a sterilization procedure, said cap having a sterilant access port therethrough to allow sterilant to enter said housing;

(b) an absorbent material in said cap assembly to substantially restrict access of condensed sterilant to the biological indicator.

50. A protective cap assembly according to claim 49, wherein the cap assembly includes a first cap portion and a second cap portion, said first cap portion being adapted at one end to couple with said open end of said tube and adapted at the other end to couple with said second cap portion.

51. A protective cap assembly according to claim 50, wherein friction fittings couple the portion of the cap assembly to each other and couple the cap assembly to the tube.

52. A protective cap assembly according to claim 50, wherein threaded fittings couple the portions of the cap assembly to each other and couple the cap assembly to the tube.

53. A protective cap assembly according to claim 50, wherein said absorbent material is in the first cap portion.

54. A protective cap assembly according to claim 49, wherein said absorbent material comprises an absorbent gum material.

55. A protective cap assembly according to claim 49, wherein said absorbent material is selected from the group consisting of guar gum, gum tragacanth, locust bean gum, gum arabic, xanthan gum, karaya gum, Gum Accroides, Gum Pontianak, and Ghatti gum, and mixtures of two or more materials in the group.

56. A protective cap assembly according to claim 49, wherein said absorbent material is Ghatti gum.

57. A protective cap assembly according to claim 49, wherein said absorbent material is a paper disc coated with a material selected from the group consisting of D(+)-cellobiose, meso-inositol, xylitol, trehalose, adonitol, polyethylene glycol, dulcitol, D-mannitol, sucrose, myoerythritol, sorbitol, and mixtures of two or more materials in the group.

* * * * *